US012806058B2

(12) United States Patent
Kazerooni et al.

(10) Patent No.: US 12,806,058 B2
(45) **Date of Patent: *Nov. 24, 2026**

(54) TRUNK SUPPORTING EXOSKELETON AND METHOD OF USE

(71) Applicant: The Regents of the University of California, Oakland, CA (US)

(72) Inventors: Homayoon Kazerooni, Berkeley, CA (US); Erich Hacker, Portland, OR (US); Lee-Huang Chen, Anaheim, CA (US)

(73) Assignee: The Regents of the University of California, Oakland, CA (US)

( * ) Notice: Subject to any disclaimer, the term of this patent is extended or adjusted under 35 U.S.C. 154(b) by 1435 days.

This patent is subject to a terminal disclaimer.

(21) Appl. No.: 17/038,328

(22) Filed: Sep. 30, 2020

(65) Prior Publication Data

US 2021/0007875 A1 Jan. 14, 2021

Related U.S. Application Data

(63) Continuation of application No. 15/469,201, filed on Mar. 24, 2017, now Pat. No. 10,821,017, which is a (Continued)

(51) Int. Cl.

*A61F 5/02* (2006.01)
*A61F 2/68* (2006.01)

(Continued)

(52) U.S. Cl.

CPC ................ *A61F 5/028* (2013.01); *A61F 2/68* (2013.01); *A61F 2/70* (2013.01); *A61F 5/02* (2013.01);

(Continued)

(58) Field of Classification Search

CPC .. A61F 5/02; A61F 5/026; A61F 5/028; A61F 2/68; A61F 2/70; A61F 2002/5038;

(Continued)

(56) References Cited

U.S. PATENT DOCUMENTS 1,202,851 A 10/1916 Kelly
1,409,326 A 3/1922 Williamson (Continued)

FOREIGN PATENT DOCUMENTS

CN 201934433 U 8/2011
JP H01274758 A 11/1989

(Continued)

OTHER PUBLICATIONS

U.S. Appl. No. 15/469,201, Notice of Allowance and Fees Due (Ptol-85), Jun. 30, 2020, 8 pgs.

(Continued)

*Primary Examiner* — Timothy A Stanis
(74) *Attorney, Agent, or Firm* — Sterne, Kessler, Goldstein & Fox P.L.L.C.

(57) ABSTRACT

An exoskeleton includes two torque generators, two thigh links, and a supporting trunk rotatably coupled to the thigh links. When a wearer bends forward in the sagittal plane such that the supporting trunk extends beyond a predetermined angle A with respect to vertical, at least one of the torque generators imposes a resisting torque between the supporting trunk and a corresponding thigh link, thus imposing a force onto a wearer's trunk and thighs to aid in supporting the wearer in a bent position. The exoskeleton may include an active or passive means for actuating the generators. When the supporting trunk does not extend beyond the predetermined angle A, the torque generators do not impose resisting torques between the supporting trunk and the thigh links during the entire range of motion of the (Continued)

thigh links, thus enabling a wearer to walk, run and sit without constraint while in an upright position.

15 Claims, 13 Drawing Sheets

Related U.S. Application Data continuation of application No. 14/125,117, filed as application No. PCT/US2012/041891 on Jun. 11, 2012, now Pat. No. 9,655,762.

(60) Provisional application No. 61/495,484, filed on Jun. 10, 2011.

(51) Int. Cl.

| | |
|---|---|
| ***A61F 2/70*** | (2006.01) |
| *A61F 2/50* | (2006.01) |
| *A61F 5/01* | (2006.01) |

(52) U.S. Cl.

CPC ...... *A61F 5/026* (2013.01); *A61F 2002/5038* (2013.01); *A61F 2002/5039* (2013.01); *A61F 2005/016* (2013.01); *A61F 2005/0169* (2013.01); *A61F 2005/0179* (2013.01); *A61F 2005/0188* (2013.01); *A61H 2201/1623* (2013.01)

(58) Field of Classification Search

CPC ........ A61F 2002/5039; A61F 2005/016; A61F 2005/169; A61F 2005/179; A61H 1/02

See application file for complete search history.

(56) References Cited

U.S. PATENT DOCUMENTS

| | | | | |
|---|---|---|---|---|
| 4,256,098 | A | 3/1981 | Swan et al. | |
| 4,745,911 | A | 5/1988 | Bender | |
| 4,829,989 | A * | 5/1989 | Deamer | A63B 21/00181 602/19 |
| 5,176,622 | A * | 1/1993 | Anderson | A61F 5/02 482/131 |
| 5,207,635 | A | 5/1993 | Richards et al. | |
| 5,259,833 | A | 11/1993 | Barnett | |
| 5,951,591 | A * | 9/1999 | Roberts | A61F 5/02 606/241 |
| 6,436,065 | B1 | 8/2002 | Mitchell | |
| 7,553,266 | B2 | 6/2009 | Abdoli-Eramaki | |
| 7,744,552 | B1 * | 6/2010 | Babcock | A61H 3/00 602/19 |
| 8,060,945 | B2 | 11/2011 | Adarraga | |
| 8,568,344 | B2 | 10/2013 | Ferguson et al. | |
| 9,022,956 | B2 | 5/2015 | Kazerooni et al. | |
| 10,821,017 | B2 | 11/2020 | Kazerooni et al. | |
| 2005/0130815 | A1 * | 6/2005 | Abdoli-Eramaki | A61F 5/026 482/121 |
| 2007/0090143 | A1 | 4/2007 | Clayton et al. | |
| 2008/0161738 | A1 * | 7/2008 | Giesen | A61F 5/026 602/19 |
| 2008/0228121 | A1 | 9/2008 | Hughes | |
| 2009/0292369 | A1 | 11/2009 | Kazerooni et al. | |
| 2010/0094185 | A1 | 4/2010 | Amundson et al. | |
| 2010/0125230 | A1 | 5/2010 | Hurley | |
| 2011/0098617 | A1 * | 4/2011 | Ferguson | A61F 5/026 602/16 |
| 2011/0105966 | A1 | 5/2011 | Kazerooni et al. | |
| 2011/0266323 | A1 | 11/2011 | Kazerooni et al. | |
| 2014/0121573 | A1 | 5/2014 | Kazerooni et al. | |

FOREIGN PATENT DOCUMENTS

| | | | |
|---|---|---|---|
| JP | 2007020672 | A | 2/2007 |
| JP | 2007097636 | A | 4/2007 |
| JP | 2007130234 | A | 5/2007 |
| JP | 2007282991 | A | 11/2007 |
| JP | 2009011818 | A | 1/2009 |
| WO | 2010011848 | A1 | 1/2010 |

OTHER PUBLICATIONS

U.S. Appl. No. 15/469,201, Examiner Interview Summary Record (Ptol-413), Jun. 30, 2020, 1 pg.

U.S. Appl. No. 15/469,201, Notice of Allowance and Fees Due (Ptol-85), Aug. 17, 2020, 5 pgs.

U.S. Appl. No. 14/125,117, Examiner Interview mailed Jan. 12, 2017, 4 pgs.

U.S. Appl. No. 14/125,117, Examiner Interview Summary mailed Mar. 23, 2016, 4 pgs.

U.S. Appl. No. 14/125,117, Final Office Action mailed Aug. 12, 2016, 19 pgs.

U.S. Appl. No. 14/125,117, Non Final Office Action mailed Jan. 11, 2016, 20 pgs.

U.S. Appl. No. 14/125,117, Notice of Allowance mailed Feb. 10, 2017, 8 pgs.

Int'l Application Serial No. PCT/US15/61284, ISRWO mailed Apr. 11, 2016, 26 pgs.

Korean Application Serial No. 10-2013-7033493, Notice of Allowance mailed Nov. 27, 2019, 5 pgs.

Korean Application Serial No. 10-2013-7033493, Office Action mailed Feb. 25, 2019, 29 pgs.

* cited by examiner

TRUNK SUPPORTING EXOSKELETON AND METHOD OF USE

CROSS-REFERENCE TO RELATED APPLICATIONS

This application is a continuation of U.S. application Ser. No. 15/469,201, filed on 2017 Mar. 24, which is a continuation of U.S. application Ser. No. 14/125,117, filed on 2013 Dec. 11, granted as U.S. Pat. No. 9,655,762 on 2017 May 23, which a 371-national phase entry application of a Patent Cooperation Treaty (PCT) Application No. PCT/US12/41891, filed on 2012 Jun. 11, which claims the benefit of U.S. Provisional Patent Application Ser. No. 61/495,484, filed 2011 Jun. 10, 2011. All of the above-referenced patent applications are incorporated herein by reference in their entirety.

TECHNICAL HELD

The present disclosure pertains to the art of support devices for the human spine, more particularly to a trunk supporting exoskeleton configured to reduce the bending moment on a person's back during a forward bend.

BACKGROUND

In general, back support devices that are configured to assist a person in bending, lifting, and/or standing upright are known in the art. U.S. Pat. Nos. 6,436,065, 5,951,591, 5,176,622, and 7,744,552. U.S. Pat. Nos. 1,409,326 and 4,829,989 describe devices where the moment is created during a bend to counteract the moments from a person's trunk gravity weight. These systems utilize a passive, spring resistance to create a torque between the wearer's torso and legs. By creating a restorative moment at the hip, the probability of injury of the L5/S 1 area of the spine is greatly reduced. Once the angle between torso and leg reaches a predetermined angle during stooping, squatting, or walking, the devices provide resistance. However, none of the devices differentiate between walking and bending or sitting and bending. This means the user cannot walk comfortably using these passive devices since the user's legs must push against the devices during walking. Similarly, the user cannot sit comfortably using these passive devices since the user's legs must push against the devices during sitting. This is uncomfortable and hazardous, preventing the user from moving around unrestricted, and is the most important reason to avoid the use of these systems in various industrial settings. Unlike the aforementioned devices, the technology described here differentiates between walking and bending and between sitting and bending. Even though the relative angle between the user's trunk and a swinging thigh is similar to each other in both cases of bending and walking (or bending and sitting), we have discovered a means by which they can be distinguished using minimal sensing and hardware.

SUMMARY

The present disclosure is directed to a trunk supporting exoskeleton configured to reduce the muscle forces in a wearer's back during the forward lumbar flexion. In general, the exoskeleton includes first and second thigh links configured to couple to a wearer's thighs, and a supporting trunk configured to be coupled to a wearer's trunk. The supporting trunk is rotatably coupled to the thigh links to allow flexion and extension of the thigh links with respect to the supporting trunk. First and second opposing torque generators selectively create torque between the supporting trunk and respective thigh links.

In operation, when a wearer bends forward in the sagittal plane such that a predetermined portion of the supporting trunk deviates or extends beyond a predetermined angle with respect to vertical, at least one of the torque generators imposes a resisting torque between the supporting trunk and a corresponding thigh link. This causes the supporting trunk to impose a force onto a wearer's trunk, and the thigh links to impose forces onto the wearer's respective thighs, thereby helping to support the wearer while in the bent position. In one embodiment, the exoskeleton includes a passive means for actuating the torque generators. More specifically, when a predetermined portion of the exoskeleton extends past the predetermined angle with respect to vertical, a resilient pendulum comes into contact with an engagement bracket, causing a resisting torque between the supporting trunk and a respective thigh link. In another embodiment, the exoskeleton includes an active means for actuating the torque generators, such as hydraulic motors, pneumatic motors, and electric motors.

The exoskeleton may include a signal processor including a controller, which produces a control signal to drive torque generators as a function of a set of input signals received by the signal processor. The input signals may be generated by one or more sensors incorporated into the exoskeleton, such as a velocity sensor, an accelerometer, a force sensor, or an angle sensor.

Importantly, when the supporting trunk does not extend beyond the predetermined angle with respect to vertical, the torque generators do not impose resisting torques between the supporting trunk and the thigh links during the entire range of wearer motion of the thigh links. Thus, a wearer is able to walk, run, and sit without any constraint while the wearer is in a substantially upright position.

DETAILED DESCRIPTION

Figure 1:
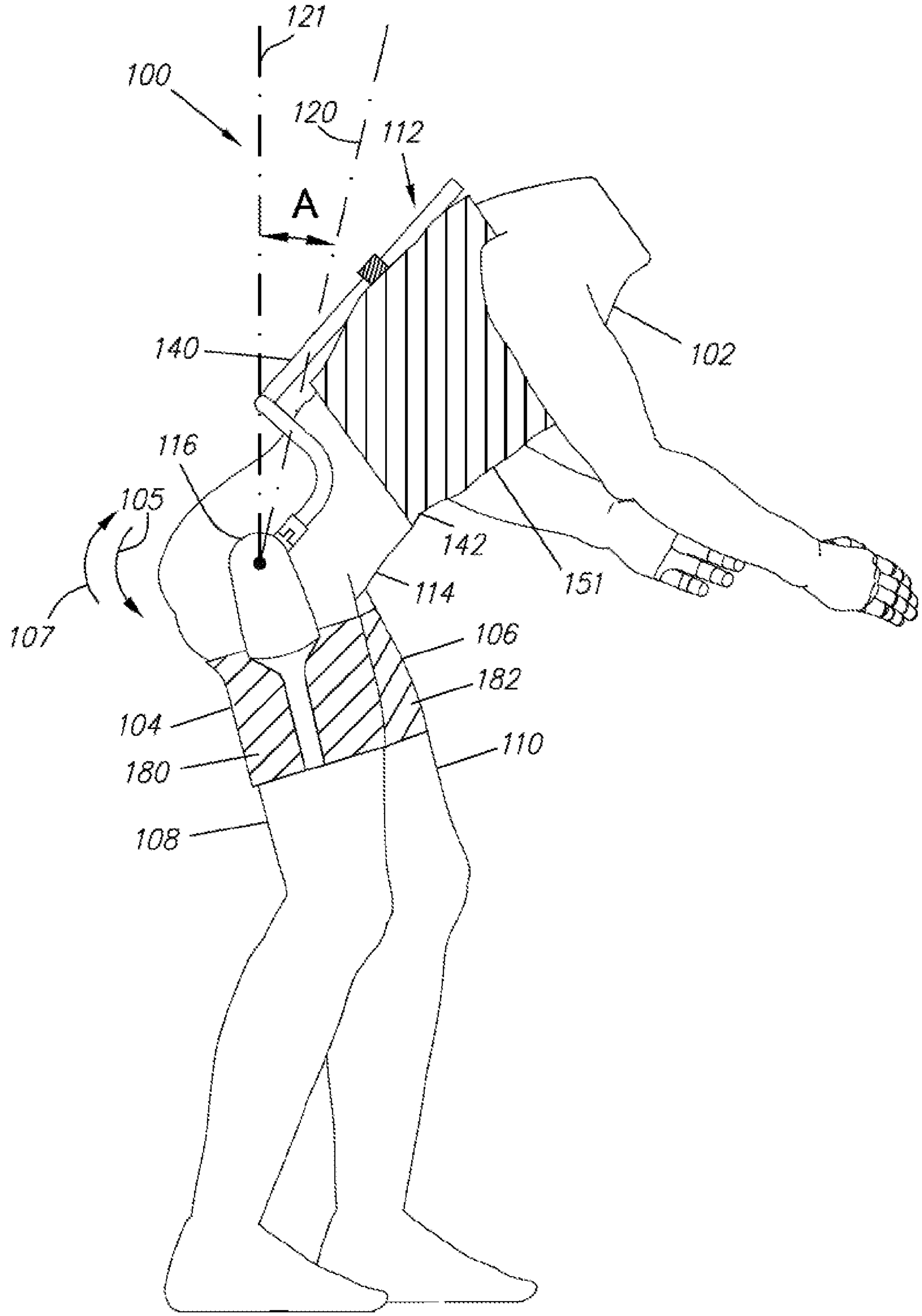
FIG. 1 depicts a trunk supporting exoskeleton on a forward-leaning wearer.

FIG. 1 illustrates a trunk supporting exoskeleton (referred to as exoskeleton from now on) 100 which is configured to be worn by a person or wearer. Exoskeleton 100, in addition to other functions, reduces the muscle forces in the wearer's back during the forward lumbar flexion. In general, exoskeleton 100 comprises two thigh links 104 and 106, which are configured to couple to a wearer's thighs 108 and 110, a supporting trunk 112, which is configured to be coupled to the person's trunk 114. Supporting trunk 112 is rotatably coupled to thigh links 104 and 106, allowing for the flexion and extension along arrows 105 and 107 of thigh links 104 and 106 with respect to supporting trunk 112. Additionally, exoskeleton 100 includes first and second opposing torque generators 116 (only one of which is depicted in FIG. 1), capable of creating torques between supporting trunk 112 and respective first and second thigh links 104 and 106.

Figure 2:
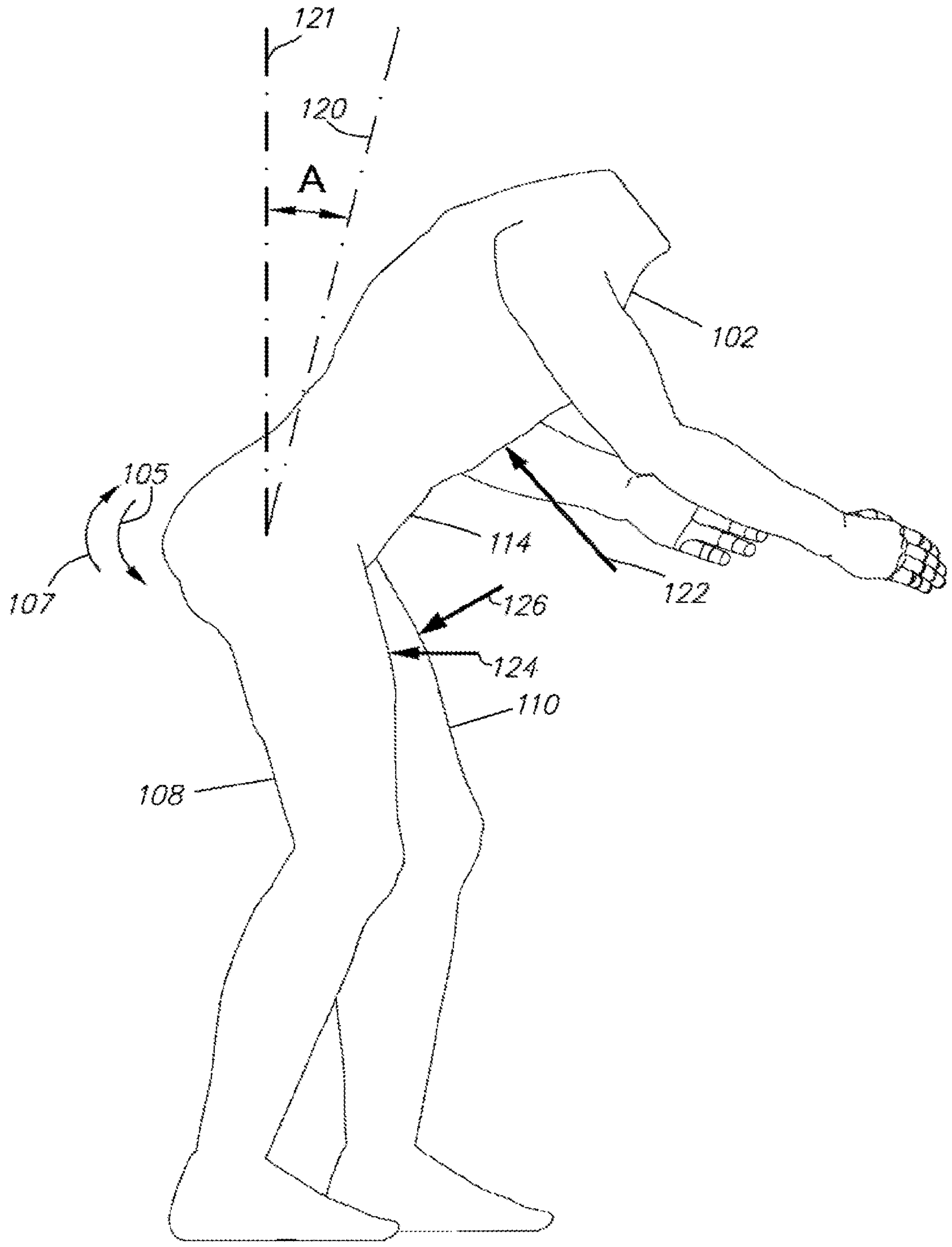
FIG. 2 depicts forces imparted on the wearer of FIG. 1, with the trunk supporting exoskeleton removed for clarity.

In operation, when a wearer bends forward in the sagittal plane such that supporting trunk 112 deviates beyond a straight line 120, at least one of torque generators 116 imposes a resisting torque between supporting trunk 112 and its corresponding thigh link 104, 106. More specifically, line 120 extends at a predetermined angle from a straight vertical line 121 and represents a point beyond which torque generators are actuated. In other words, during the forward lumbar flexion, when supporting trunk 112 extends beyond a predetermined angle from vertical, torque is imposed on thigh links 104, 106. As shown in FIG. 2, this device causes supporting trunk 112 to impose a force 122 onto a wearer's trunk 114, and thigh links 104, 106 to impose forces 124 and 126 onto the wearer's respective thighs 108 and 110. It should be understood that exoskeleton 100 can be configured such that torque is imposed on thigh links 104, 106 when a predetermined portion of supporting trunk 112 extends beyond a predetermined angle from vertical. In some embodiments, torque may be imposed when any portion of trunk 112 extends beyond line 120. In general, exoskeleton 100 can be configured such that torque is imposed on thigh links 104, 106 when supporting trunk 112 shapes itself into a generally bent configuration.

Figure 3:
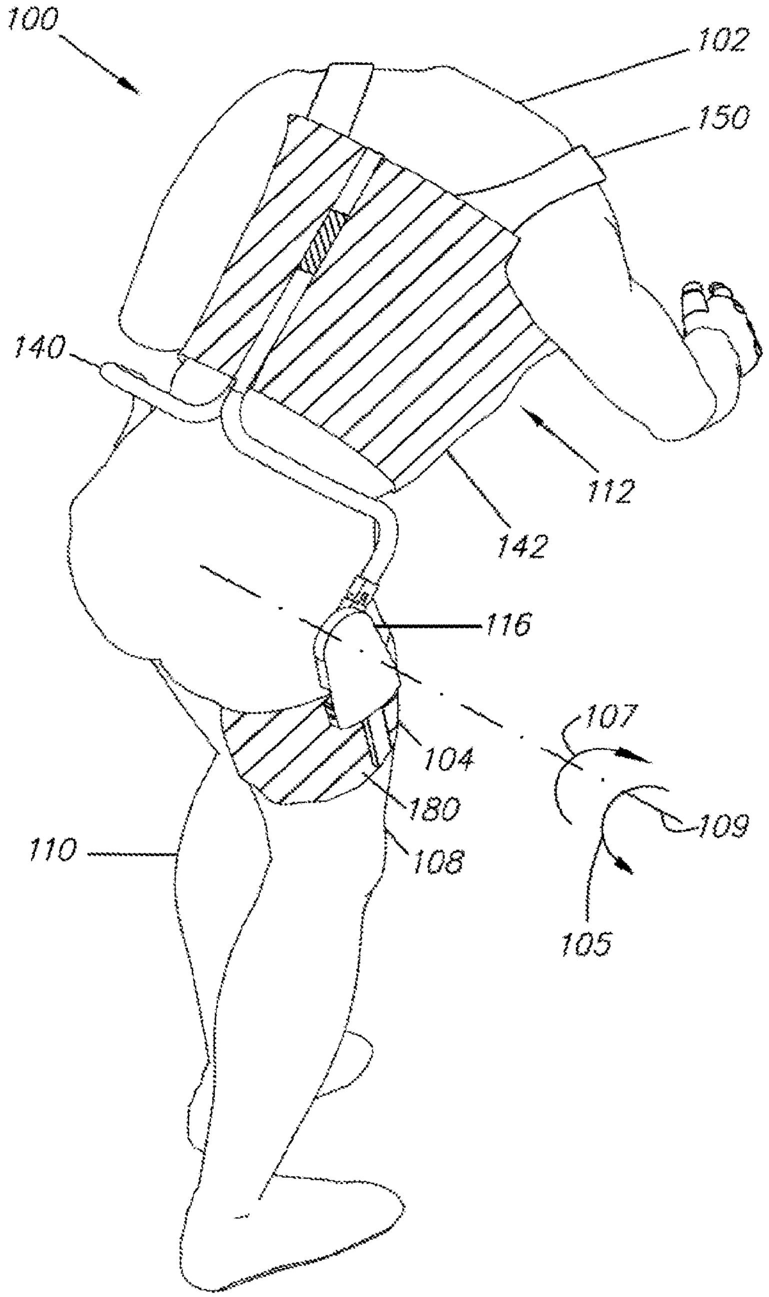
FIG. 3 depicts a back perspective view of a trunk supporting exoskeleton.

Further, in operation, when supporting trunk 112 is not deviated from line 120, torque generators 116 impose no resisting torques between supporting trunk 112 and thigh links 104 and 106 during the entire range of motion of thigh links 104 and 106. This is a unique characteristic of this device where the person can walk, run and sit without any constraint as long as the person's trunk is substantially vertically aligned (i.e. not bent or not deviated beyond line 120). Torque generators 116 have unique characteristics where they only provide resisting torque when the human trunk is bent more than a predetermined value of an angle A, regardless of the human thighs angles with respect to the human trunk 114. As long as the person's trunk does not extend beyond line 120, regardless of the person's legs positions and posture, no torque is generated by the torque generators 116. FIG. 3 is a perspective view where the flexion and extension of thigh link 104 with respect to supporting trunk 112 along axis 109 is depicted clearly.

Figure 4:
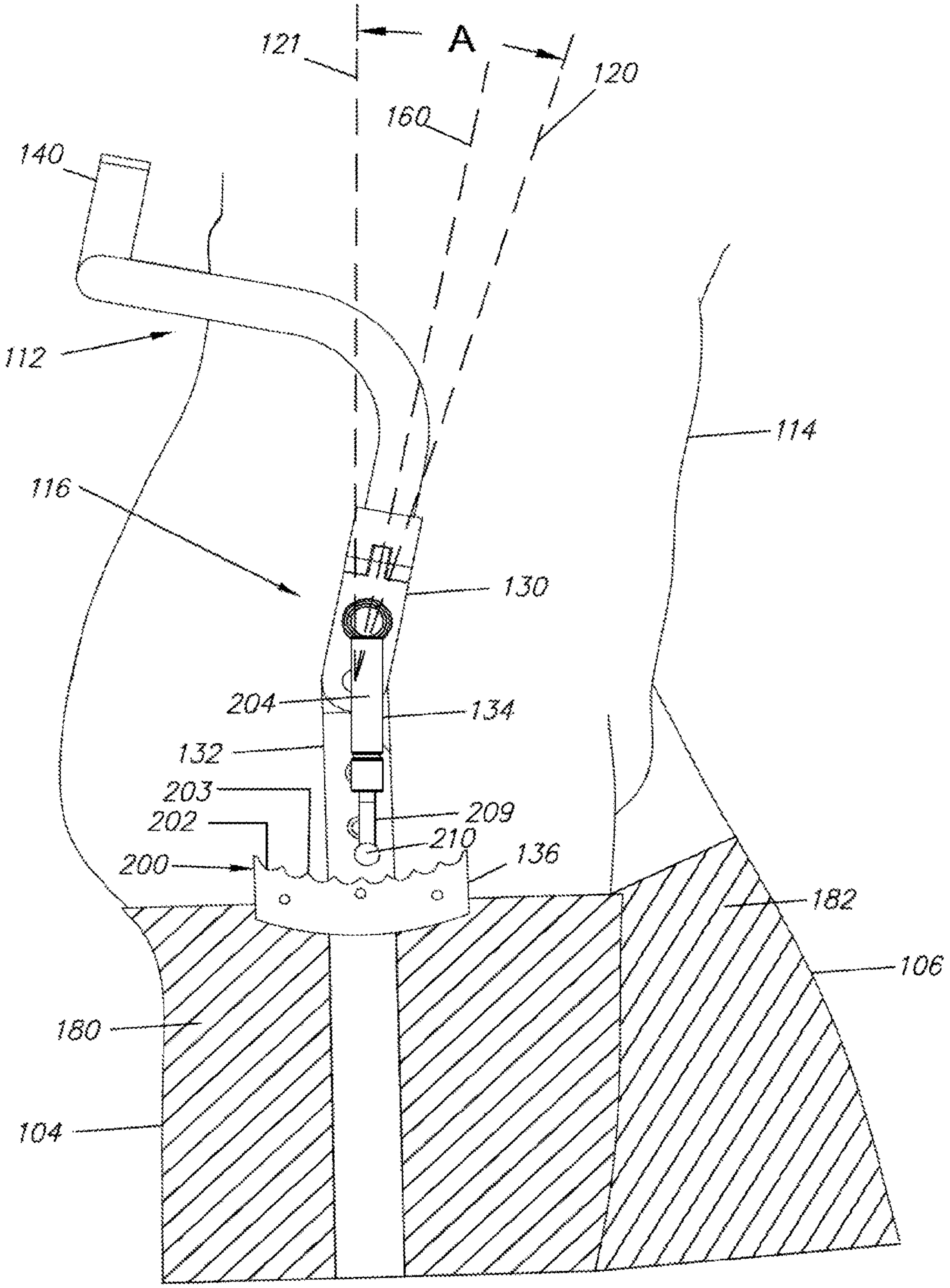
FIG. 4 is a side view of a passive torque generator embodiment in an unengaged position.
Figure 5:
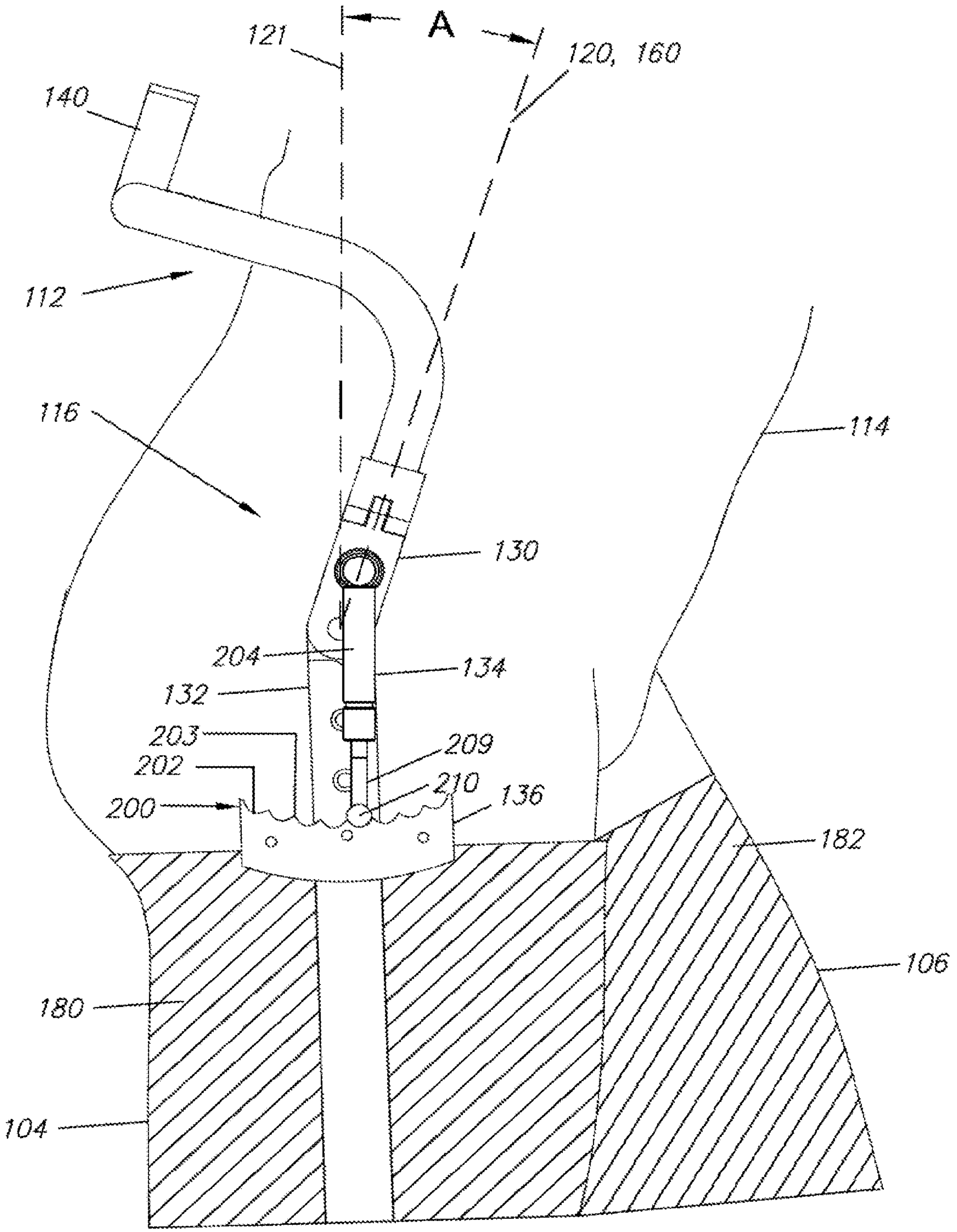
FIG. 5 is a side view of the passive torque generator of FIG. 4 in a first engaged position.

FIG. 4 describes an embodiment of torque generators 116 where respective covers have been removed. It should be noted that torque generators 116 are identical to each other and therefore, only the torque generator shown in FIG. 4 will be discussed in detail. As shown, torque generator 116 comprises an upper bracket 130 coupled to trunk support 112, a lower bracket 132 coupled to thigh link 104 and rotatably coupled in a sagittal plane to upper bracket 130, a resilient pendulum 134 which is rotatably mounted on upper bracket 130, and an engagement bracket 136 which is securely coupled onto lower bracket 132. In operation, when a predetermined portion of upper bracket 130 extends past line 120, as depicted in FIG. 5, resilient pendulum 134 comes into contact with engagement bracket 136, causing a resisting torque between upper bracket 130 and lower bracket 132. When upper bracket 130 is not deviated from line 120, as depicted in FIG. 4, resilient pendulum 134 will not be in contact with engagement bracket 136, and no resisting torque is produced between upper bracket 130 and lower bracket 132. In some embodiments, resilient pendulum 134 behaves like a compression spring where deflections result in compression forces. In some embodiments, engagement bracket 136 and lower bracket 132 are a one-piece part.

Figure 6:
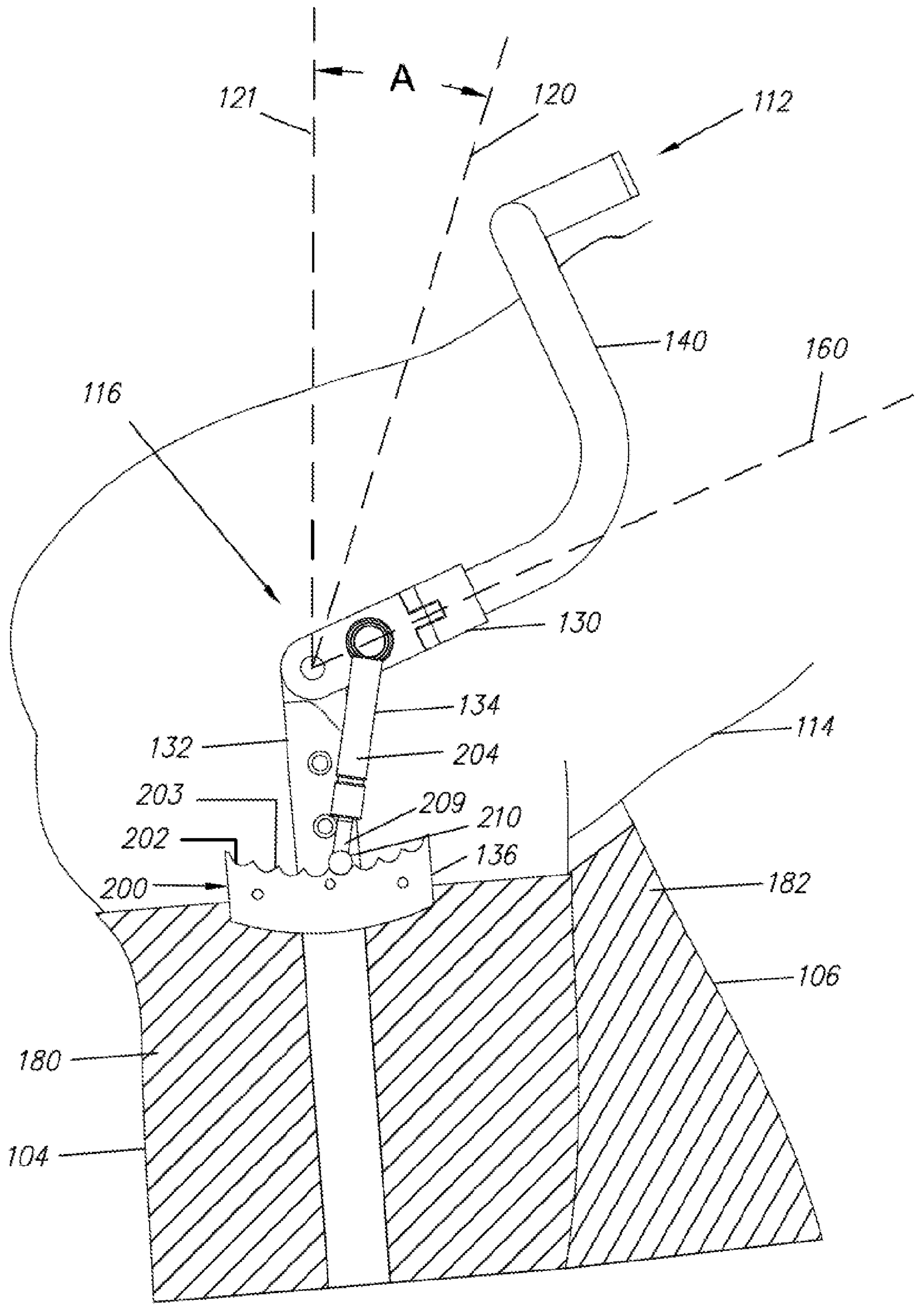
FIG. 6 is a side view of the passive torque generator of FIG. 4 in a second engaged position.

FIG. 6 shows a situation where a person has bent at the waist substantially and resilient pendulum 134 is compressed, such that the length is shortened substantially. In some embodiments shown in FIG. 4, FIG. 5, and FIG. 6, resilient pendulum 134 comprises an air spring comprising cylinder 204 and piston 209 moving relative to each other. In some embodiments, resilient pendulum 134 is a coil spring. Engagement bracket 136 has a profile that does not allow the tip of resilient pendulum 134 to slide relative to bracket 136. In the depicted embodiment, engagement bracket 136 has a profile that matches the circular profile of the tip of the resilient pendulum 134. More specifically, engagement bracket 136 includes a scalloped upper wall 200 including a plurality of curved divots 202 separated by peaks 203. Resilient pendulum 134 further includes a tip or stop device 210 in the form of a round knob sized to fit within each of the curved divots 202. As depicted in FIG. 5, when a wearer bends beyond a predetermined point represented by line 120, stop device 210 engages with one of curved divots 202 and is held in position by peaks 203, such that, upon further bending of the wearer, the resilient pendulum 134 will be held in place and the resilient pendulum 134 will compress. In some embodiments, top upper wall 200 and/or tip 210 may include a frictional surface to prevent the sliding motion of the tip 210 within a curved divot 202.

In some embodiments, torque generators 116 are active systems. Examples of active torque generators which can be utilized include, without limitation, hydraulic motors, pneumatic motors, and electric motors, including, without limitation, alternating current (AC) motors, brush-type direct current (DC) motors, brushless DC motors, electronically commutated motors (ECMs), stepping motors, and combinations thereof. In some embodiments, torque generators 116 each include an electric motor and a transmission. The resistance supplied by first and second torque generators 116 between supporting trunk 112 and respective thigh links 104 and 106 impose a force onto the person's trunk 114 in the manner depicted in FIG. 1. These torques also cause thigh links 104 and 106 to impose forces onto the person's thighs 108 and 110.

Figure 10:
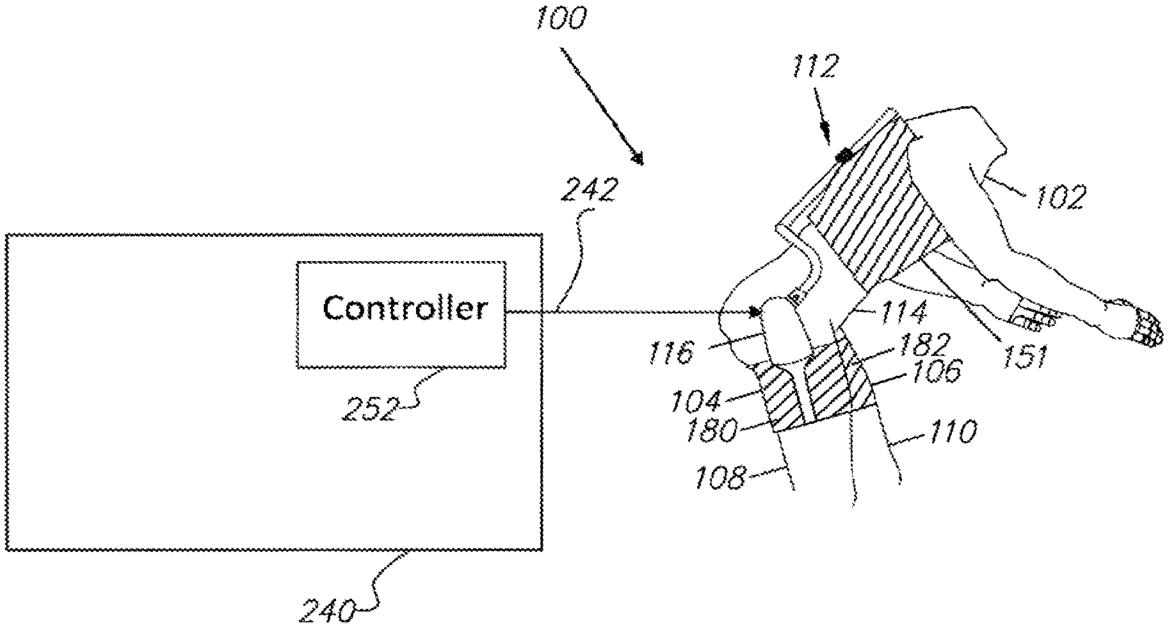
FIG. 10 depicts a signal processor.
Figure 11:
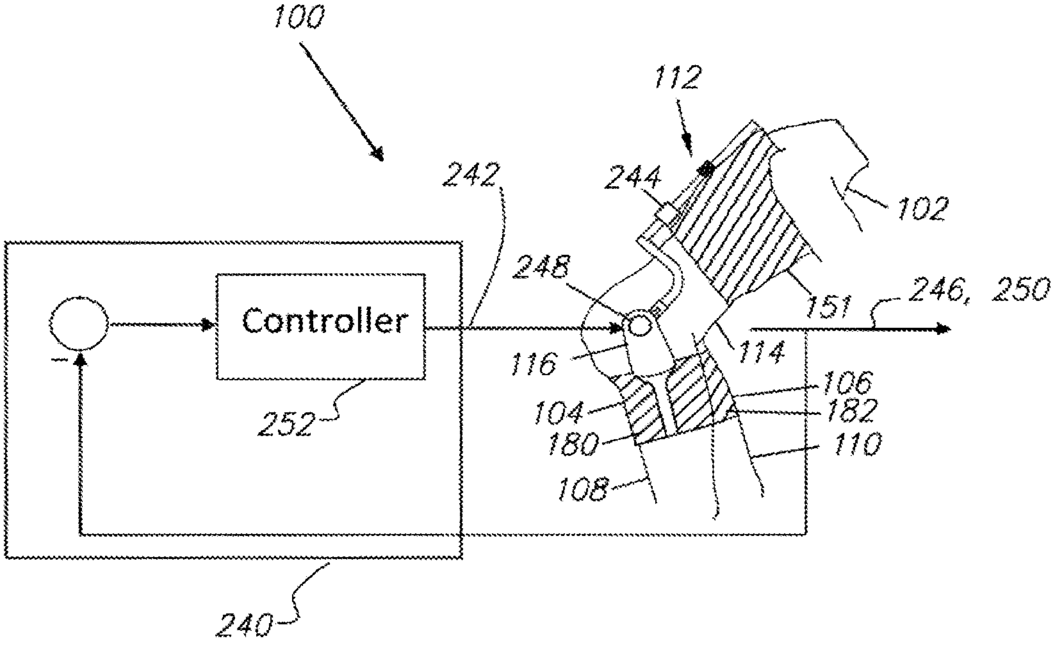
FIG. 11 depicts a first method of control.

The manner in which the resistance torque can be automatically adjusted when an active torque generator is used will now be discussed with reference to FIGS. 10-12. In some embodiments, as shown in FIG. 10, exoskeleton 100 includes a signal processor 240 configured to produce a control signal 242 for torque generators 116, wherein control signal 242 drives torque generators 116. Signal processor 240 incorporates a controller 252 which produces control signal 242 for torque generators 116 as a function of a set of input signals that signal processor 240 receives. Examples of input signals that signal processor 240 receives include, without limitation, signals representing angles of thigh links 104 and 106 with respect to supporting trunk 112, signals representing the velocity of supporting trunk 112 with respect to thigh links 104 and 106, signals representing the acceleration of supporting trunk 112 with respect to thigh links 104 or 106, a signal representing the absolute angle of supporting trunk 112, a signal representing the absolute velocity of supporting trunk 112, a signal representing the absolute acceleration of supporting trunk 112, a signal representing at least one torque generator's movement, a signal representing at least one torque generator's speed, a signal representing at least one torque generator's acceleration, a signal representing at least one torque generator's torque, a signal representing at least one torque generator's force, a signal representing the person's movement, a signal representing the person's bending angle, a signal representing the person's bending velocity, a signal representing the person's bending acceleration, a signal representing the contact force between person 102 and supporting trunk 112, a signal representing an electromyography (EMG) signal from said person and combinations thereof.

Various sensors can be utilized to provide controller 252 with the necessary signal information. In one preferred embodiment depicted in FIG. 11, supporting trunk 112 includes a first sensor 244 generating a first signal 246 representing output from first sensor 244. In one example, first sensor 244 is an absolute angle sensor and first signal 246 is an absolute angle signal representing the angle that person 102 or supporting trunk 112 has bent forward relative to line 120 or line 121 (shown in FIG. 1). However, it should be understood that first sensor 244 could be a velocity sensor, an accelerometer, or other type of movement sensor. Supporting trunk 112 can also include a second sensor 248 (shown in FIG. 11) generating a second signal 250 representing an output from second sensor 248. In one example, second sensor 248 is an angle sensor and second signal 250 is an angle signal representing the angle of supporting trunk 112 with respect to thigh links 104 or 106, In general, second sensor 248 is either included in the torque generators 116 or installed on the same location on thigh links 104 or 106 or supporting trunk 112 that torque generator 116 are installed on. However, it should also be understood that second sensor 248 can be a torque generator movement sensor, a torque generator speed sensor, a torque generator accelerometer, a torque generator torque or force sensor, or any type of standard movement sensor. In operation, as shown in FIG. 11, signal processor 240 produces control signal 242 for torque generators 116 as a function of first signal 246 and/or second signal 250. That is, controller 252 utilizes first and second signals 246 and 250 as a feedback signal to generate control signal 242. The type of controller utilized dictates the magnitude of the resistance torque. One can find a variety of algorithms for controller 252 to perform the indicated task. In general, controllers with large gains lead to large resistance torques, while controllers with small gains result in smaller resistance torque.

Figure 12:
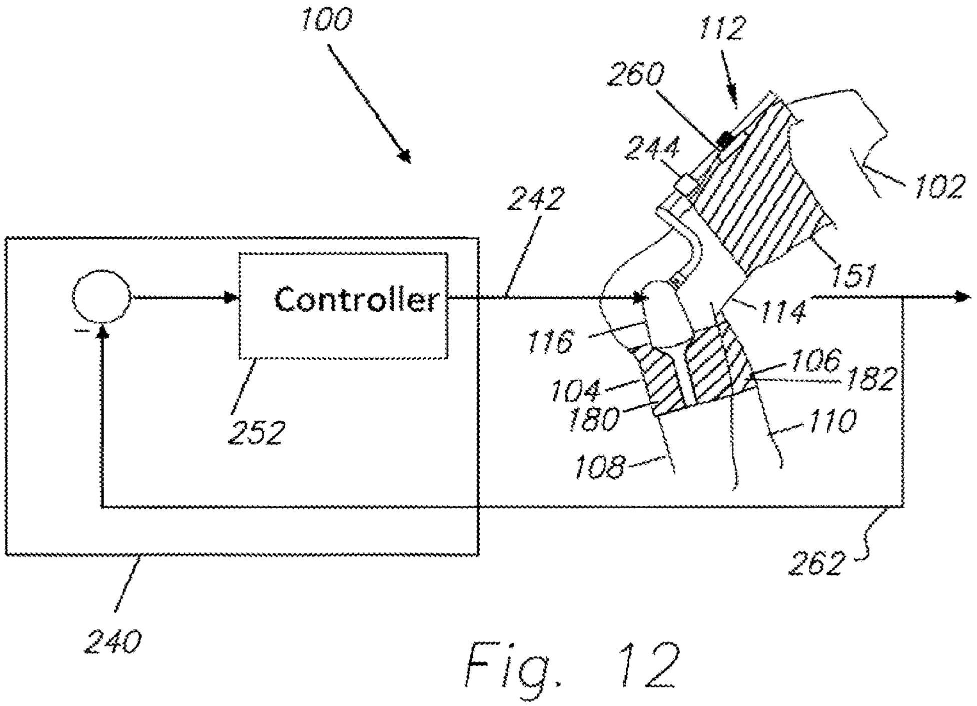
FIG. 12 depicts an alternative method of control.

As shown in FIG. 12, exoskeleton 100 may also include a force or pressure sensor 260 generating a force or pressure signal 262 representing the force or pressure between person 102 and supporting trunk 112. In operation, signal processor 240 produces control signal 242 for torque generators 116 as a function of force or pressure signal 262. That is, controller 252 utilizes force or pressure signal 262 as a feedback signal to generate control signal 242.

From the discussion above, it should be understood that controller 252 can be programmed and configured to activate torque generators 116 in a variety of ways based on signals 246, 250 and/or 262 from sensors 244, 248 and/or 260. In some embodiments, the resistance torque is a function of how much person 102 is bending forward. For example, in some embodiments, the resistance torque increases as person bends forward. In some embodiments, the resistance torque is a function of the angle between person 102 and a line 120. In some embodiments, the resistance torque increases linearly as the angle between person 102 and vertical line 121 (shown in FIG. 2) increases. In some embodiments, the resistance torque is a function of how much supporting trunk 112 moves toward thigh links 104 or 106. In some embodiments, the resistance torque is a function of the angle between supporting trunk 112 and vertical line 121. In some embodiments, the resistance torque increases linearly as the angle between supporting trunk 112 and vertical line 121 increases. In some embodiments, the controller is configured to adjust the resistance torque imposed by the first and second torque generators to be generally constant for at least one segment of a bending movement of a wearer.

In some embodiments, as shown in FIG. 1 and FIG. 3, supporting trunk 112 comprises a human interface 142, which is configured to be coupled to a person's trunk 114, and a frame 140, which is configured to be coupled to human interface 142. Frame 140 is rotatably coupled to thigh links 104 and 106 allowing for extension and flexion of thigh links 104 and 106 relative to frame 140. Frame 140 comprises any material or combination of materials capable of performing the indicated functions. Examples of materials of frame 140 include, without limitation, aluminum materials, plastic materials, carbon fiber materials, metallic materials, and combinations thereof. In some embodiments, frame 140 comprises a plurality of components coupled or hinged to each other.

Figure 7:
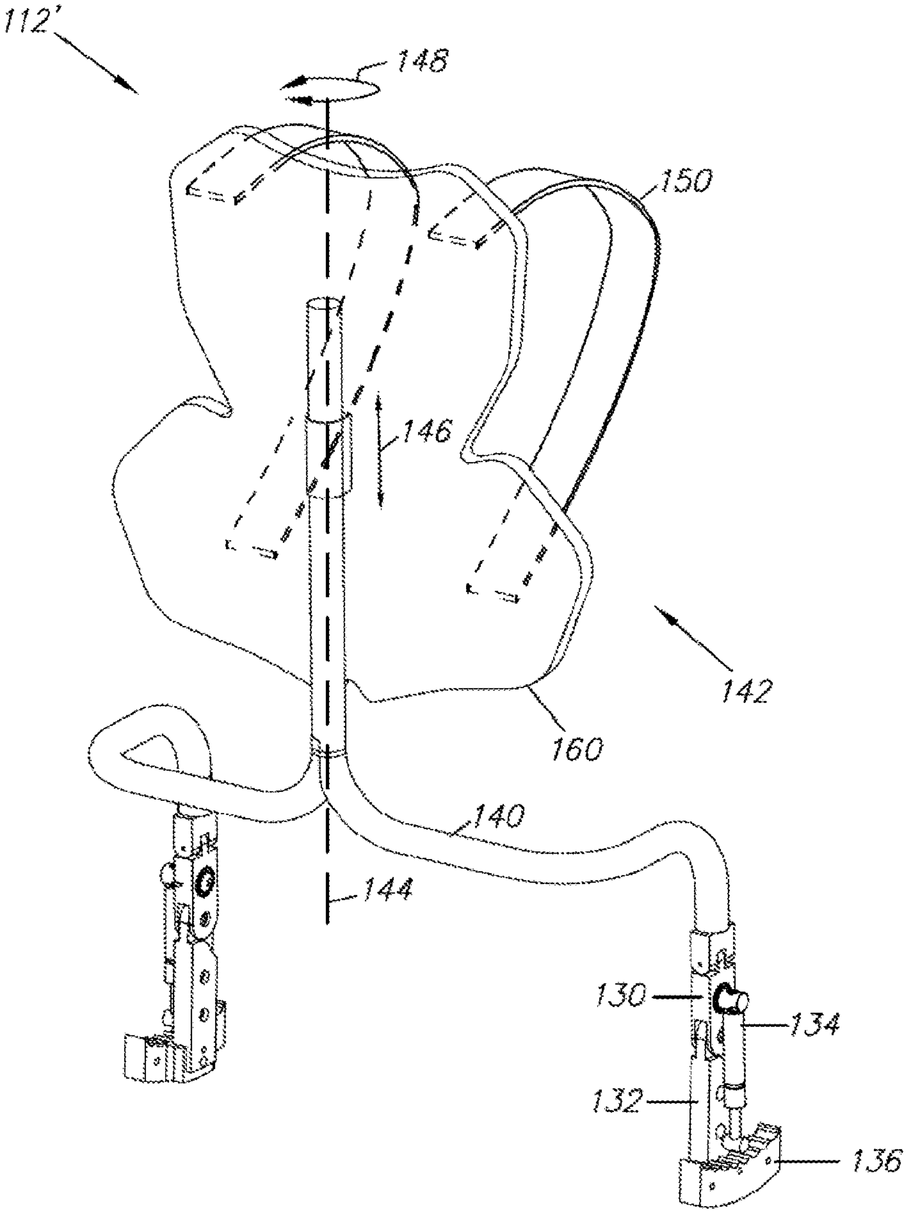
FIG. 7 depicts a human interlace embodiment of the supporting trunk.

In some embodiments, a support trunk 112' includes human interface 142 comprises a back panel 160 to interface the person's back, as depicted in FIG. 7. In some embodiments, back panel 160 is complaint and deforms as the person bends. In some embodiments, human interface 142 further comprises at least one shoulder strap 150 configured to couple to the person. Referring back to the embodiment of FIG. 1, the disclosure may also include a front panel 151 adapted to engage the front of a wearer's trunk 114, to provide additional support. Human interface 142 comprises any material or combination of materials capable of performing the indicated functions. Examples of materials of human interface 142 include, without limitation, fabric materials, plastic materials, belts, leather materials, carbon fiber materials, metallic materials, and combinations thereof.

In some embodiments, as shown in FIG. 7, human interface 142 is slidable along axis 144 with respect to frame 140 (i.e. slidable along a length of frame 140), This sliding movement, shown by arrow 146, facilitates the bending maneuver of the wearer.

In some embodiments, as shown in FIG. 7, human interface 142 is rotatable around axis 144 with respect to frame 140. Arrow 148 shows this rotational movement. This rotation allows the person to twist his/her upper body without moving their legs.

Figure 8:
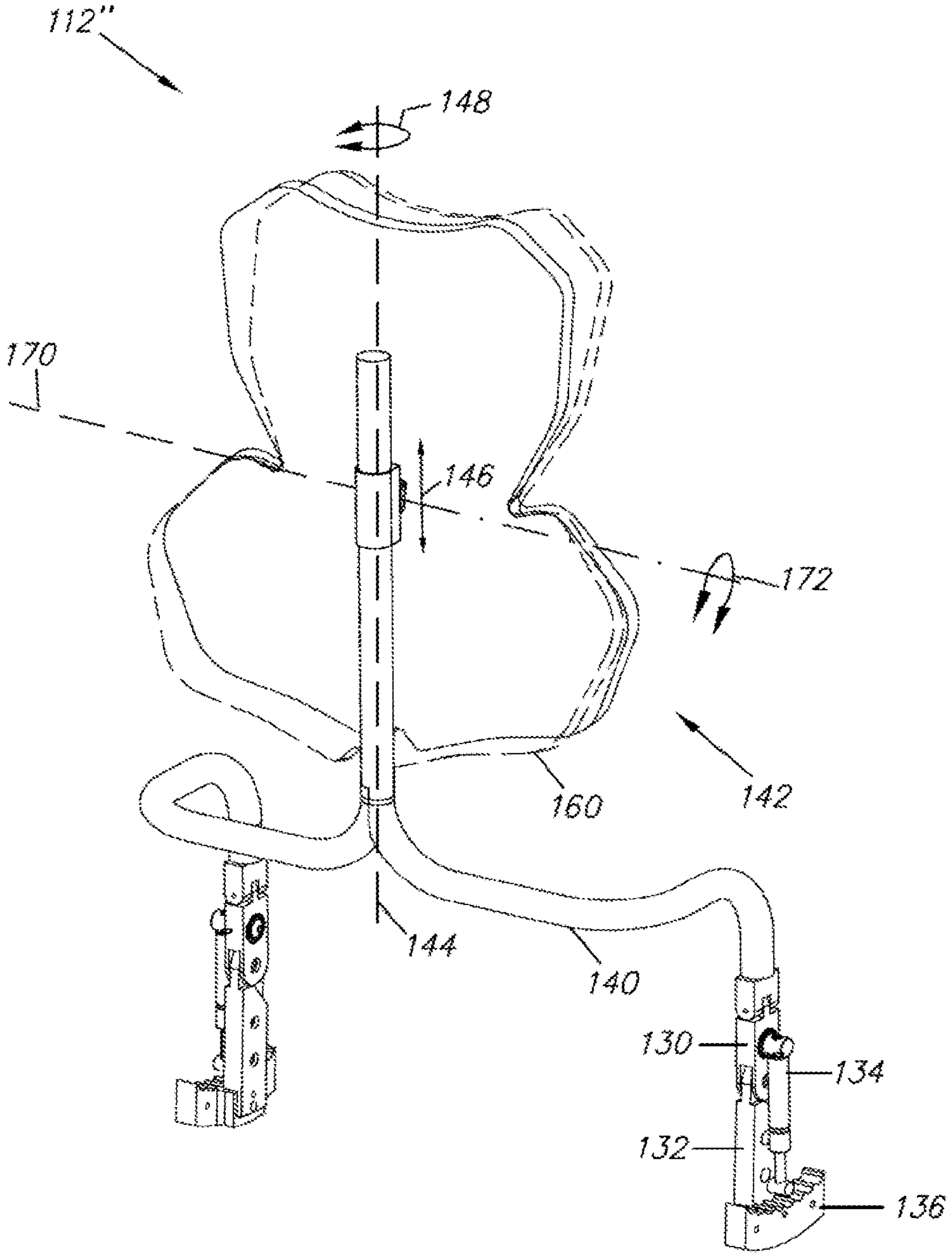
FIG. 8 depicts another human interface embodiment of the supporting trunk.

In some embodiments, as shown in FIG. 8, a support trunk 112" includes human interface 142 is rotatable around axis 170 with respect to frame 140. Arrow 172 shows this rotational movement. This rotation facilitates the bending maneuver of the person.

Figure 13:
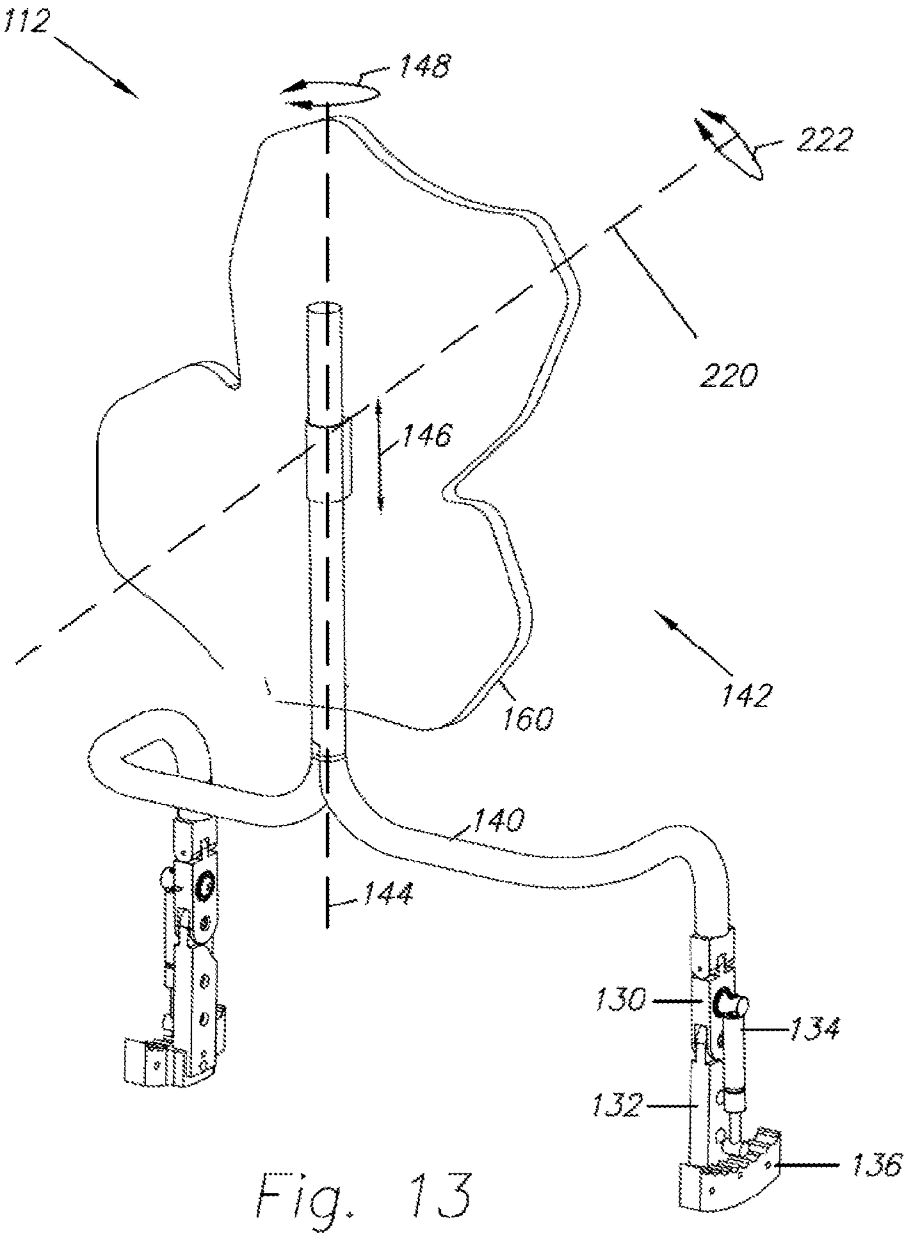
FIG. 13 depicts another human interface embodiment of the supporting trunk.

In some embodiments, as shown in FIG. 13, human interface 142 is rotatable around axis 220 with respect to frame 140. Arrow 222 shows this rotational movement. This rotation facilitates the rotational maneuver of the person.

In some embodiments, thigh links 104 and 106 each further comprise at least one thigh strap 180 and 182 configured to couple to person's thighs 108 and 110, as depicted in Figures. Thigh straps 180 and 182 comprise any material or combination of materials capable of performing the indicated functions. Examples of materials of thigh straps 180 and 182 include, without limitation, fabric materials, plastic materials, belts, leather materials, carbon fiber materials, metallic materials, and combinations thereof.

Figure 9:
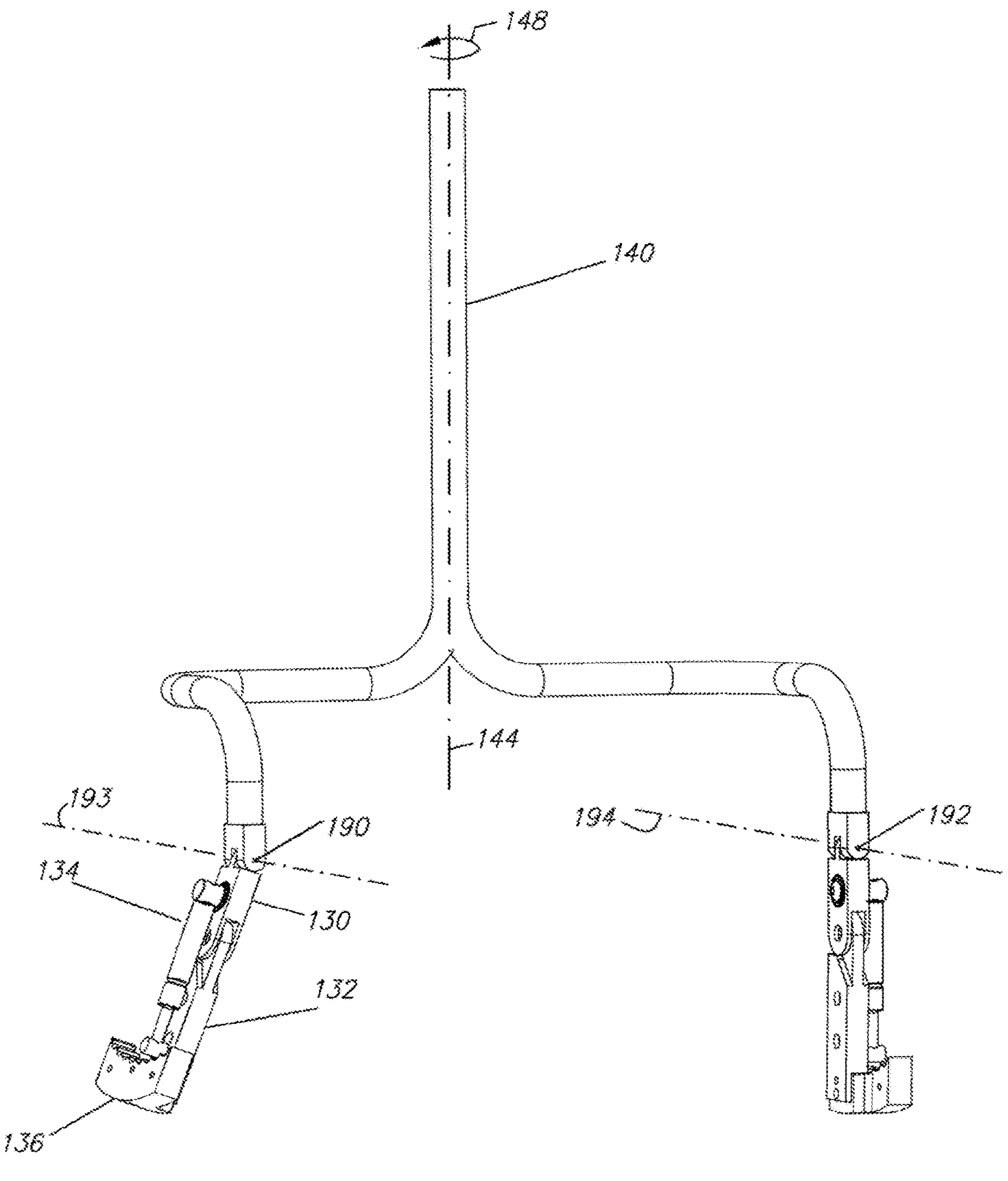
FIG. 9 depicts a portion of the exoskeleton embodiment with abduction and adduction capability.

In some embodiments, as shown in FIG. 9, frame 140 further comprises two rotary abduction-adduction joints 190 and 192 allowing for abduction and adduction of respective thigh links 104 and 106 relative to supporting trunk 112. As shown in FIG. 9, axes 193 and 194 represent the axes of abduction and adduction joints. FIG. 9 shows a portion of supporting trunk 112 where thigh link 104 has abducted.

Although described with reference to some embodiments, it should be readily understood that various changes and/or modifications can be made to the disclosed embodiments without departing from the spirit thereof. For instance, the various human interface, thigh straps and torque generators can be combined in various ways to form different overall embodiments. In general, the disclosure is only intended to be limited by the scope of the following claims.

What is claimed is:

1. A trunk supporting exoskeleton configured to be worn by a person to reduce muscle forces in a back of the person during forward bending, the trunk supporting exoskeleton comprising:

a supporting trunk configured to be coupled to a trunk of the person, wherein the supporting trunk comprises:

at least one of a back panel configured to interface with a back of the person or a front panel configured to interface a front of the person;

a human interface configured to be coupled to the trunk of the person; and a frame configured to be coupled to the human interface, wherein the frame is rotatably coupled to first and second thigh links, and wherein the human interface is rotatable with respect to the frame;

wherein the first and second thigh links are rotatably coupled to the supporting trunk and are configured to move in unison with thighs of the person; and first and second torque generators, wherein:

when the person bends forward in a sagittal plane, at least one of the first and second torque generators imposes a resisting torque between the supporting trunk and at least one of the first and second thigh links, and when the person does not bend forward, the first and second torque generators automatically cease to impose any resisting torques between the supporting trunk and the first and second thigh links through an entire range of motion of the first and second thigh links.

2. The trunk supporting exoskeleton of claim 1, wherein the supporting trunk further comprises first and second rotary abduction-adduction joints enabling abduction and adduction of the first and second thigh links relative to the supporting trunk.

3. The trunk supporting exoskeleton of claim 1, wherein the supporting trunk comprises at least one shoulder strap configured to be coupled to the person.

4. The trunk supporting exoskeleton of claim 1, wherein at least one of the first and second torque generators comprises:

a resilient pendulum rotatably coupled to the supporting trunk; and an engagement bracket coupled to one of the first and second thigh links, wherein:

when the supporting trunk bends forward, the resilient pendulum comes into contact with the engagement bracket, causing a resisting torque between the supporting trunk and at least one of the first and second thigh links, and when the supporting trunk does not bend forward, the resilient pendulum is not in contact with the engagement bracket and does not impose resisting torque between the supporting trunk and at least the one of the first and second thigh links.

5. The trunk supporting exoskeleton of claim 1, wherein the human interface is rotatable with respect to an axis that is transverse to a longitudinal axis of the frame.

6. A trunk supporting exoskeleton configured to be worn by a person to reduce muscle forces in a back of the person during forward bending, the trunk supporting exoskeleton comprising:

a supporting trunk configured to be coupled to a trunk of the person, wherein the supporting trunk comprises:

at least one of a back panel configured to interface with a back of the person or a front panel configured to interface a front of the person;

a human interface configured to be coupled to a trunk of the person; and a frame configured to be coupled to the human interface, wherein the frame is rotatably coupled to two thigh links, and wherein the human interface is rotatable with respect to the frame;

wherein the two thigh links are configured to couple to the thighs of the person and rotatably coupled to the supporting trunk; and a first torque generator and a second torque generator, wherein the first and second torque generators each generate torque between the supporting trunk and one of the two thigh links only when the supporting trunk is shaped into a bent configuration, and wherein the first torque generator operates independently of the second torque generator and automatically ceases to impose any resisting torque when the person does not bend forward and performs walking, running, and sitting motions.

7. The trunk supporting exoskeleton of claim 6, wherein the supporting trunk further comprises first and second rotary abduction-adduction joints, enabling abduction and adduction of the two thigh links relative to the supporting trunk.

8. The trunk supporting exoskeleton of claim 6, wherein the supporting trunk comprises at least one shoulder strap configured to be coupled to the person.

9. The trunk supporting exoskeleton of claim 6, wherein the at least torque generator comprises:

a resilient pendulum rotatably coupled to the supporting trunk; and an engagement bracket coupled to one of the first and second thigh links, wherein:

when the supporting trunk bends forward, the resilient pendulum comes into contact with the engagement bracket, causing a resisting torque between the supporting trunk and at least one of the two thigh links, and when the supporting trunk does not bend forward, the resilient pendulum is not in contact with the engagement bracket and does not impose the resisting torque between the supporting trunk and the at least one of the two thigh links.

10. The trunk supporting exoskeleton of claim 6, wherein the human interface is rotatable with respect to an axis that is transverse to a longitudinal axis of the frame.

11. A trunk supporting exoskeleton configured to be worn by a person, the trunk supporting exoskeleton comprising:

a supporting trunk configured to be coupled to a trunk of the person, wherein the supporting trunk comprises:

at least one of a back panel configured to interface with a back of the person or a front panel configured to interface a front of the person;

a human interface configured to be coupled to the trunk of the person; and a frame configured to be coupled to the human interface, wherein the frame is rotatably coupled to first and second thigh links, and wherein the human interface is rotatable with respect to the frame;

wherein the first and second thigh links are rotatably coupled to the supporting trunk and are configured to move in unison with thighs of the person; and a torque generator, wherein:

when the person bends forward in a sagittal plane, the torque generator imposes a resisting torque between the supporting trunk and at least one of the first and second thigh links, and when the person is not bent forward, the torque generator automatically ceases to impose any resisting torques between the supporting trunk and the first and second thigh links through an entire range of motion of the first and second thigh links.

12. The trunk supporting exoskeleton of claim 11, wherein the supporting trunk further comprises first and second rotary abduction-adduction joints, enabling abduction and adduction of the first and second thigh links relative to the supporting trunk.

13. The trunk supporting exoskeleton of claim 11, wherein the supporting trunk comprises at least one shoulder strap, configured to be coupled to the person.

14. The trunk supporting exoskeleton of claim 11, wherein the torque generator comprises:

a resilient pendulum rotatably coupled to the supporting trunk; and an engagement bracket coupled to one of the first and second thigh links, wherein:

when the supporting trunk bends forward, the resilient pendulum comes into contact with the engagement bracket, causing a resisting torque between the supporting trunk and the one of the first and second thigh links, through an entire range of motion of the first and second thigh links, and when the supporting trunk does not bend forward, the resilient pendulum is not in contact with the engagement bracket and does not impose resisting torque between the supporting trunk and the one of the first and second thigh links, through an entire range of motion of the first and second thigh links.

15. The trunk supporting exoskeleton of claim 11, wherein the human interface is rotatable with respect to an axis that is transverse to a longitudinal axis of the frame.

* * * * *